United States Patent
Zelder et al.

(10) Patent No.: US 8,741,623 B2
(45) Date of Patent: Jun. 3, 2014

(54) PROCESS FOR THE PRODUCTION OF CADAVERINE

(75) Inventors: Oskar Zelder, Speyer (DE); Weol Kyu Jeong, Jeollabuk-do (KR); Corinna Klopprogge, Mannheim (DE); Andrea Herold, Ketsch (DE); Hartwig Schröder, Nußloch (DE)

(73) Assignee: BASF SE, Ludwigshafen (DE)

( * ) Notice: Subject to any disclaimer, the term of this patent is extended or adjusted under 35 U.S.C. 154(b) by 581 days.

(21) Appl. No.: 12/295,348

(22) PCT Filed: Mar. 23, 2007

(86) PCT No.: PCT/EP2007/052783
§ 371 (c)(1),
(2), (4) Date: Sep. 30, 2008

(87) PCT Pub. No.: WO2007/113127
PCT Pub. Date: Oct. 11, 2007

(65) Prior Publication Data
US 2009/0246838 A1    Oct. 1, 2009

(51) Int. Cl.
*C12N 1/20* (2006.01)
*C12N 15/74* (2006.01)
*C12N 15/77* (2006.01)
*A01N 63/00* (2006.01)
*C07H 21/04* (2006.01)

(52) U.S. Cl.
USPC ..... 435/252.32; 435/471; 435/487; 424/93.2; 424/245.1; 536/23.2; 536/23.7

(58) Field of Classification Search
USPC ......... 424/93.2, 245.1; 435/252.32, 471, 487; 536/23.2, 23.7
See application file for complete search history.

(56) References Cited

U.S. PATENT DOCUMENTS

2005/0003497 A1* 1/2005 Nishi et al. .................. 435/128

FOREIGN PATENT DOCUMENTS

| CN | 1192242 A | 9/1998 |
| JP | 2002223770 | 8/2002 |
| JP | 2004222569 | 8/2004 |
| JP | 2004222569 A * | 8/2004 |

OTHER PUBLICATIONS

Azevedo, 2002, Amino Acids, 22: 217-230.*
Schmidt-Glenewinkle et al., 1977, Neurochemical Research, 2: 619-637.*
Low et al., 1999, Nature Biotechnology, 17: 37-41.*
Jetten et al., 1995, Appl. Microbiol. Biotechnol. 43: 76-82.*
Kalinowski et al., 2003, Journal of Biotechnology, 104: 5-25.*
Wittich et al., 1989, Biochem J. 1989, 260:265-269.*
Nakagawa et al., 2001, Geneseq Accession No. AAH68529, computer printout, p. 7-9.*
Bewley et al., Feb. 2006, PNAS, vol. 103, No. 7, p. 2063-2068.*
Abo-Dalo et al., 2004, Biochemical Journal, vol. 384, p. 129-137.*
Qian et al., 2011, Biotechnology and Bioengineering, vol. 108, No. 1, p. 93-103.*
Wosnick, M. A. et al., "Rapid Construction of Large Synthetic Genes: Total Chemical Synthesis of Two Different Versions of the Bovine Prochymosin Gene", Gene, 1987, vol. 60, pp. 115-127.
"Gene Synthesis: Assembly of Target Sequences Using Mutually Priming Long Oligonucleotides", Unit 8.2B in "Short Protocols in Molecular Biology", Ausubel, F. M., et al., Eds., John Wiley & Sons, Inc., 1995, pp. 8-8-8-10.
Schmidt-Glenewinkel, Y. N., et al., "The Conversion of Lysine into Piperidine, Cadaverine, and Pipecolic Acid in the Brain and Other Organs of the Mouse", Neurochemical Research, 1977, vol. 2, pp. 619-637.
Kikuchi, Y., et al., "Characterization of a Second Lysine Decarboxylase Isolated from *Escherichia coli*", Journal of Bacteriology, 1997, vol. 179, No. 14, pp. 4486-4492.

* cited by examiner

*Primary Examiner* — Shin-Lin Chen
(74) *Attorney, Agent, or Firm* — Drinker Biddle & Reath LLP

(57) ABSTRACT

Process for the production of cadaverine by constructing a recombinant microorganism which has a deregulated lysine decarboxylase gene and at least one deregulated gene selected from the group (i) which consists of aspartokinase, aspartatesemialdehyde dehydrogenase, dihydrodipicolinate synthase, dihydrodipicolinate reductase, tetrahydrodipicolinate succinylase, succinyl-amino-ketopimelate transaminase, succinyl-diamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase, homoserine dehydrogenase, phophoenolpyruvate carboxykinase, succinyl-CoA synthetase, methylmalonyl-CoA mutase, provided that if aspartokinase is deregulated as gene (i) at least a second gene (i) other than aspartokinase has to be deregulated, and cultivating said microorganism.

15 Claims, No Drawings

US 8,741,623 B2

PROCESS FOR THE PRODUCTION OF CADAVERINE

RELATED APPLICATIONS

This application is a national stage application (under 35 U.S.C. 371) of PCT/EP2007/052783, filed Mar. 23, 2007, which claims benefit of European application 06112029.1, filed Mar. 30, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_00750. The size of the text file is 18 KB, and the text file was created on Sep. 30, 2008.

FIELD OF THE INVENTION

The present invention relates to a process for the production of cadaverine. More particularly, this invention relates to the use of recombinant microorganism comprising DNA molecules in a deregulated form which are essential to produce cadaverine.

PRIOR ART

JP 2002223770 discloses a method for producing cadaverine by introducing a lysine decarboxylation gene and/or a lysine-cadaverine antiporter gene into a lysine producing microorganism.

JP 2004222569 discloses a method for producing cadaverine by culturing recombinant coryneform bacteria having L-lysine decarboxylase activity and homoserine auxotrophy.

SUMMARY OF THE INVENTION

In one aspect, the present invention provides a process for the production of cadaverine by constructing a recombinant microorganism which has a deregulated lysine decarboxylase and at least one deregulated gene selected from genes which are essential in the lysine biosynthetic pathway, and cultivating said microorganism.

In another aspect, the present invention provides a process for the production of polyamides comprising a step as mentioned above for the production of cadaverine and reacting that cadaverine with a dicarboxylic acid.

DETAILED DESCRIPTION OF THE INVENTION

In the description that follows, a number of terms are utilized extensively. Definitions are herein provided to facilitate understanding of the invention.

The term cadaverine means 1,5-diaminopentane.

Promoter. A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent, if the promoter is a constitutive promoter.

Enhancer. A promoter element. An enhancer can increase the efficiency with which a particular gene is transcribed into mRNA irrespective of the distance or orientation of the enhancer relative to the start site of transcription.

Expression. Expression is the process by which a polypeptide is produced from a structural gene. The process involves transcription of the gene into mRNA and the translation of such mRNA into polypeptide(s).

Cloning vector. A DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Expression vector. A DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

Recombinant host. A recombinant host may be any prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989) ["Sambrook"].

As used herein, a substantially pure protein means that the desired purified protein is essentially free from contaminating cellular components, as evidenced by a single band following polyacrylamide-sodium dodecyl sulfate gel electrophoresis (SDS-PAGE). The term "substantially pure" is further meant to describe a molecule which is homogeneous by one or more purity or homogeneity characteristics used by those of skill in the art. For example, a substantially pure lysine decarboxylase will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of lysine decarboxylase with other compounds. In addition, the term is not meant to exclude lysine decarboxylase fusion proteins isolated from a recombinant host.

In a first aspect, the present invention provides a process for the production of cadaverine by constructing a recombinant microorganism which has a deregulated lysine decarboxylase gene and at least one deregulated gene selected from the group (i) which consists of aspartokinase, aspartatesemialdehyde dehydrogenase, dihydrodipicolinate synthase, dihydrodipicolinate reductase, tetrahydrodipicolinate succinylase, succinylamino-ketopimelate transaminase, succinyl-diamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase, homoserine dehydrogenase, phophoenolpyruvate carboxykinase, succinyl-CoA synthetase, methylmalonyl-CoA mutase, provided that if aspartokinase is deregulated as gene (i) at least a second gene (i) other than aspartokinase has to be deregulated, and cultivating said microorganism.

The methodologies of the present invention feature recombinant microorganisms, preferably including vectors or genes (e.g., wild-type and/or mutated genes) as described herein and/or cultured in a manner which results in the production of cadaverine.

The term "recombinant" microorganism includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived.

The term "deregulated" includes expression of a gene product (e.g., lysine decarboxylase) at a level lower or higher than that expressed prior to manipulation of the microorganism or in a comparable microorganism which has not been manipulated. In one embodiment, the microorganism can be genetically manipulated (e.g., genetically engineered) to express a level of gene product at a lesser or higher level than that expressed prior to manipulation of the microorganism or in a comparable microorganism which has not been manipulated. Genetic manipulation can include, but is not limited to, altering or modifying regulatory sequences or sites associated with expression of a particular gene (e.g., by removing strong promoters, inducible promoters or multiple promoters), modifying the chromosomal location of a particular gene, altering nucleic acid sequences adjacent to a particular gene such as a ribosome binding site or transcription terminator, decreasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, or other methods to knock-out or block expression of the target protein).

The term "deregulated gene activity", e.g. deregulated lysine decarboxylase, also means that a gene activity, e.g. a lysine decarboxylase activity, is introduced into a microorganism where the respective gene activity, e.g. the lysine decarboxylase activity, has not been observed before, e.g. by introducing a heterologous gene, e.g. a lysine decarboxylase gene in one or more copies into the microorganism preferably by means of genetic engineering.

Lysine decarboxylase catalyzes the decarboxylation of L-lysine into cadaverine. The enzyme has been classified as E.C. 4.1.1.18. The enzymes isolated from *Escherichia coli* having lysine decarboxylase activity are the cadA gene product (Kyoto Encyclopedia of Genes and Genomes, Entry b4131) and the ldcC gene product (Kyoto Encyclopedia of Genes and Genomes, Entry JW0181).

The amino acid sequences of *E. coli* cadA is disclosed in SEQ ID NO:1 and of *E. coli* ldcC is disclosed in SEQ ID NO:2.

DNA molecules encoding the *E. coli* lysine decarboxylase gene can be obtained by screening cDNA or genomic libraries with polynucleotide probes having nucleotide sequences reverse-translated from the amino acid sequence of SEQ ID NO:1 or 2.

Alternatively, the *E. coli* lysine decarboxylase genes can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., Gene 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize DNA molecules at least 2 kilobases in length. Adang et al., Plant Molec. Biol. 21:1131 (1993); Bambot et al., PCR Methods and Applications 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., PCR Methods Appl. 4:299 (1995).

Variants of *E. coli* lysine decarboxylase can be produced that contain conservative amino acid changes, compared with the parent enzyme. That is, variants can be obtained that contain one or more amino acid substitutions of SEQ ID NO:1 or 2, in which an alkyl amino acid is substituted for an alkyl amino acid in the lysine decarboxylase amino acid sequence, an aromatic amino acid is substituted for an aromatic amino acid in the *E. coli* lysine decarboxylase amino acid sequence, a sulfur-containing amino acid is substituted for a sulfur-containing amino acid in the *E. coli* lysine decarboxylase amino acid sequence, a hydroxy-containing amino acid is substituted for a hydroxy-containing amino acid in the *E. coli* lysine decarboxylase amino acid sequence, an acidic amino acid is substituted for an acidic amino acid in the *E. coli* lysine decarboxylase amino acid sequence, a basic amino acid is substituted for a basic amino acid in the *E. coli* lysine decarboxylase amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) cysteine and methionine, (4) serine and threonine, (5) aspartate and glutamate, (6) glutamine and asparagine, and (7) lysine, arginine and histidine.

Conservative amino acid changes in the *E. coli* lysine decarboxylase can be introduced by substituting nucleotides for the nucleotides recited in SEQ ID NO:1 or NO:2. Such "conservative amino acid" variants can be obtained, for example, by oligonucleotide-directed mutagenesis, linker-scanning mutagenesis, mutagenesis using the polymerase chain reaction, and the like. Ausubel et al., supra, at pages 8.0.3-8.5.9; Ausubel et al. (eds.), SHORT PROTOCOLS IN MOLECULAR BIOLOGY, 3rd Edition, pages 8-10 to 8-22 (John Wiley & Sons, Inc. 1995). Also see generally, McPherson (ed.), DIRECTED MUTAGENESIS: A PRACTICAL APPROACH, IRL Press (1991). The ability of such variants to convert L-lysine to cadaverine can be determined using a standard enzyme activity assay, such as the assay described herein.

Preferred lysine decarboxylases according to the invention are the lysine decarboxylase from *E. coli* and their equivalent genes, which have up to 80%, preferably 90% and most preferred 95% and 98% sequence identity (based on amino acid sequence) with the corresponding "original" gene product and have still the biological activity of lysine decarboxylase. These equivalent genes can be easily constructed by introducing nucleotide substitutions, deletions or insertions by methods known in the art.

Another preferred embodiment of the invention are the lysine decarboxylases of *E. coli* (SEQ ID NO:1 and NO:2) which are retranslated into DNA by applying the codon usage of *Corynebacterium glutamicum*. These lysine decarboxylase polynucleotide sequences are useful for expression of lysine decarboxylase in microorganism of the genus *Corynebacterium*, especially *C. glutamicum*.

In addition to the deregulated lysine decarboxylase gene the microorganism according to the invention must have at least one deregulated gene selected from the group (i). The group (i) is a group of genes which play a key role in the biosynthesis of lysine and consists of the genes of aspartokinase, aspartatesemialdehyde dehydrogenase, dihydrodipicolinate synthase, dihydrodipicolinate reductase, tetrahydrodipicolinate succinylase, succinyl-amino-ketopimelate transaminase, succinyl-diamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase, homoserine dehydrogenase, phophoenolpyruvate carboxykinase, succinyl-CoA synthetase, methylmalonyl-CoA mutase.

At least one gene of the group (i) has to be deregulated according to the inventive process. Preferably more than one gene of group (i), e.g. two, three, four, five, six, seven, eight, nine, ten genes are deregulated in the microorganism according to the invention.

The genes and gene products of group (i) are known in the art. EP 1108790 discloses mutations in the genes of homoserinedehydrogenase and pyruvatecarboxylase which have a beneficial effect on the productivity of recombinant *corynebacteria* in the production of lysine. WO 00/63388 discloses mutations in the gene of aspartokinase which have a beneficial effect on the productivity of recombinant *corynebacteria* in the production of lysine. EP 1108790 and WO 00/63388 are incorporated by reference with respect to the mutations in these genes described above.

In the table below for every gene/gene product possible ways of deregulation of the respective gene are mentioned. The literature and documents cited in the row "Deregulation" of the table are herewith incorporated by reference with respect to gene deregulation. The ways mentioned in the table are preferred embodiments of a deregulation of the respective gene.

TABLE 1

| Enzyme (gene product) | Gene | Deregulation |
|---|---|---|
| Aspartokinase | ask | Releasing feedback inhibition by point mutation (Eggeling et al., (eds.), Handbook of *Corynebacterium glutamicum*, pages 20.2.2 (CRC press, 2005)) and amplification) |
| Aspartatesemialdehyde dehydrogenase | asd | Amplification |
| Dihydrodipicolinate synthase | dapA | Amplification |
| Dihydrodipicolinate reductase | dapB | Amplification |
| Tetrahydrodipicolinate succinylase | dapD | Amplification |
| Succinyl-amino-ketopimelate transaminase | dapC | Amplification |
| Succinyl-diamino-pimelate desuccinylase | dapE | Amplification |
| Diaminopimelate dehydrogenase | ddh | Amplification |
| Diaminopimelate epimerase | dapF | Amplification |
| Arginyl-tRNA synthetase | argS | Amplification |
| Diaminopimelate decarboxylase | lysA | Amplification |
| Pyruvate carboxylase | pycA | Releasing feedback inhibition by point mutation (EP1108790) and amplification |
| Phosphoenolpyruvate carboxylase | ppc | Amplification |
| Glucose-6-phosphate dehydrogenase | zwf | Releasing feedback inhibition by point mutation (US2003/0175911) and amplification |
| Transketolase | tkt | Amplification |
| Transaldolase | tal | Amplification |
| 6-Phosphogluconolactonase | pgl | Amplification |
| Fructose 1,6-biphosphatase | fbp | Amplification |
| Homoserine dehydrogenase | hom | Attenuating by point mutation (EP1108790) |
| Phophoenolpyruvate carboxykinase | pck | Knock-out or silencing by mutation or others |
| Succinyl-CoA synthetase | sucC | Attenuating by point mutation (WO 05/58945) |
| Methylmalonyl-CoA mutase | | Attenuating by point mutation (WO 05/58945) |

A preferred way of deregulation of the genes of aspartokinase, aspartatesemialdehyde dehydrogenase, dihydrodipicolinate synthase, dihydrodipicolinate reductase, tetrahydrodipicolinate succinylase, succinyl-amino-ketopimelate transaminase, succinyldiamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase is an "up"-mutation which increases the gene activity e.g. by gene amplification using strong expression signals and/or point mutations which enhance the enzymatic activity.

A preferred way of deregulation of the genes of homoserine dehydrogenase, phophoenolpyruvate carboxykinase, succinyl-CoA synthetase, methylmalonyl-CoA mutase is a "down"-mutation which decreases the gene activity e.g. by gene deletion or disruption, using weak expression signals and/or point mutations which destroy or decrease the enzymatic activity.

If aspartokinase is deregulated as a member of gene (i) group at least a second gene (i) member—other than aspartokinase—has to be deregulated also.

It has been observed that a significant portion of the cadaverine produced in the microorganism according to the inventive process is acetylated. In order to block this acetylation reaction which is attributed to an acetyl-CoA dependent diamine acetyltransferase and in order to increase the yield of cadaverine it is a preferred embodiment of the invention to deregulate the diamine acetyltransferase of the producing microorganism, especially to decrease its activity, e.g by deletion or disruption of the gene.

To express the deregulated genes according to the invention, the DNA sequence encoding the enzyme must be operably linked to regulatory sequences that control transcriptional expression in an expression vector and then, introduced into either a prokaryotic or eukaryotic host cell. In addition to transcriptional regulatory sequences, such as promoters and enhancers, expression vectors can include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, Ipp-lacλ-pr, phoA, gal, trc and lacZ promoters of *E. coli*, the α-amylase and the $\sigma^{28}$-specific promoters of *B. subtilis*, the promoters of the bacteriophages of *Bacillus*, *Streptomyces* promoters, the int promoter of bacteriophage lambda, the bla promoter of the Plactamase gene of pBR322, and the CAT promoter of the chloramphenicol acetyl trans-ferase gene. Prokaryotic promoters are reviewed by Glick, J. Ind. Microbiol. 1:277 (1987); Watson et al., MOLECULAR BIOLOGY OF THE GENE, 4th Ed., Benjamin Cummins (1987); Ausubel et al., supra, and Sambrook et al., supra.

A preferred promoter for the expression of the *E. coli* lysine decarboxylase is the sodA promoter of *C. glutamicum*.

Methods for expressing proteins in prokaryotic hosts are well-known to those of skill in the art. See, for example, Williams et al., "Expression of foreign proteins in *E. coli* using plasmid vectors and purification of specific polyclonal antibodies," in DNA CLONING 2: EXPRESSION SYSTEMS, 2nd Edition, Glover et al. (eds.), pages 15-58 (Oxford University Press 1995). Also see, Ward et al., "Genetic Manipulation and Expression of Antibodies," in MONOCLONAL ANTIBODIES: PRINCIPLES AND APPLICATIONS, pages 137-185 (Wiley-Liss, Inc. 1995); and Georgiou, "Expression of Proteins in Bacteria," in PROTEIN ENGINEERING: PRINCIPLES AND PRACTICE, Cleland et al. (eds.), pages 101-127 (John Wiley & Sons, Inc. 1996).

An expression vector can be introduced into bacterial host cells using a variety of techniques including calcium chloride transformation, electroporation, and the like. See, for example, Ausubel et al. (eds.), SHORT PROTOCOLS IN MOLECULAR BIOLOGY, 3rd Edition, pages 1-1 to 1-24 (John Wiley & Sons, Inc. 1995).

An important aspect of the present invention involves cultivating or culturing the recombinant microorganisms described herein, such that a desired compound cadaverine is produced. The term "cultivating" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid media) comprising nutrients essential or beneficial to the maintenance and/or growth of the microorganism.

Carbon sources which may be used include sugars and carbohydrates, such as for example glucose, sucrose, lactose, fructose, maltose, molasses, starch and cellulose, oils and fats, such as for example soy oil, sunflower oil, peanut oil and coconut oil, fatty acids, such as for example palmitic acid, stearic acid and linoleic acid, alcohols, such as for example glycerol and ethanol, and organic acids, such as for example acetic acid. In a preferred embodiment, glucose, fructose or sucrose are used as carbon sources. These substances may be used individually or as a mixture.

Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium must furthermore contain metal salts, such as for example magnesium sulfate or iron sulfate, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during cultivation.

Preferably, microorganisms of the present invention are cultured under controlled pH. The term "controlled pH" includes any pH which results in production of the desired fine chemical, e.g., cadaverine. In one embodiment, microorganisms are cultured at a pH of about 7. In another embodiment, microorganisms are cultured at a pH of between 6.0 and 8.5. The desired pH may be maintained by any number of methods known to those skilled in the art. For example, basic compounds such as sodium hydroxide, potassium hydroxide, ammonia, or ammonia water, or acidic compounds, such as phosphoric acid or sulfuric acid, are used to appropriately control the pH of the culture.

Also preferably, microorganisms of the present invention are cultured under controlled aeration. The term "controlled aeration" includes sufficient aeration (e.g., oxygen) to result in production of the desired fine chemical, e.g., cadaverine. In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermentor) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents such as fatty acid polyglycol esters).

Moreover, microorganisms of the present invention can be cultured under controlled temperatures. The term "controlled temperature" includes any temperature which results in production of the desired fine chemical, e.g., cadaverine. In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation medium is added continuously to a fermentor and an equal amount of used or "conditioned" medium is simultaneously removed, preferably for recovery of the desired cadaverine. A variety of such processes have been developed and are well-known in the art.

The methodology of the present invention can further include a step of recovering aldaverine. The term "recovering" cadaverine includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example cadaverine can be recovered from culture media by first removing the microorganisms. The broth removed biomass is then passed through or over a cation exchange resin to remove unwanted cations and then through or over an anion exchange resin to remove unwanted inorganic anions and organic acids having stronger acidities than cadaverine.

In another aspect, the present invention provides a process for the production of polyamides (e.g. Nylon®) comprising a step as mentioned above for the production of cadaverine. The cadaverine is reacted in a known manner with di-, tri- or polycarboxylic acids to get polyamides. Preferably the cadaverine is reacted with dicarboxylic acids containing 4 to 10 carbons such as succinic acid, glutaric acid, adipic acid, pimelic acid, suberic acid, azelaic acid, sebacic acid, and so forth. The dicarboxylic acid is preferably a free acid.

EXAMPLES

1. Cloning of the Lysine Decarboxylase Gene

PCR primers, WKJ12/WKJ13 and WKJ35/WKJ34, were used with the chromosomal DNA of *E. coli* as a template to amplify the DNA fragments containing cadA and IdcC gene, respectively. The amplified DNA fragments were purified, digested with restriction enzymes, Asp718/NdeI for cadA and XhoI/SpeI for IdcC, and ligated to the pClik5aMCS vector digested with same restriction enzymes resulting in pClik5aMCS cadA and pClik5aMCS IdcC, respectively.

To increase expression of the IdcC gene, *C. glutamicum* sodA promoter (Psod) was substituted in front of start codon of the gene. The DNA fragments containing the sodA promoter and coding region of the IdcC gene were amplified from each chromosomal DNA using PCR primers, WKJ31/OLD47 for Psod and WKJ33/WKJ34 for IdcC, and used as a template for fusion PCR with primers WKJ31/WKJ34. The fused PCR fragment was purified, digested with XhoI and SpeI, and inserted between XhoI and SpeI cleavage sites of the pClik5aMCS vector to construct pClik5aMCS Psod-IdcC.

Oligonucleotide Primers Used:

| | | |
|---|---|---|
| WKJ12 | caagctccttcgagctggca | (SEQ ID NO: 3) |
| WKJ13 | gggtaacgtaaaccagagaa | (SEQ ID NO: 4) |
| WKJ31 | gagagagactcgagtagctgccaattattccggg | (SEQ ID NO: 5) |
| WKJ33 | acgaaaggatttttttacccatgaacatcattgccattatg | (SEQ ID NO: 6) |
| WKJ34 | ctctctctcactagtgctcaatcacatattgccca | (SEQ ID NO: 7) |
| WKJ35 | gagagagactcgagccggaagcgatggcggcatc | (SEQ ID NO: 8) |
| OLD47 | gggtaaaaaatcctttcgtag | (SEQ ID NO: 9) |

2. Construction of Cadaverine Production Strain

To construct a cadaverine production strain, a lysine producer LU11271, which was derived from *C. glutamicum* wild type strain ATCC13032 by incorporation of a point mutation T311I into the aspartokinase gene, duplication of the diaminopimelate dehydrogenase gene and disruption of the phosphoenolpyruvate carboxykinase gene, was transformed with the recombinant plasmids having the lysine decarboxylase genes.

3. Cadaverine Production in Shaking Flask Culture

Shaking flask experiments were performed on the recombinant strains to test the cadaverine production. The same culture medium and conditions as lysine production were employed as described in WO2005059139. For the control host strain and recombinant strain having pClik5aMCS were tested in parallel. The strains were pre-cultured on CM agar overnight at 30° C. Cultured cells were harvested in a microtube containing 1.5 ml of 0.9% NaCl and cell density was determined by the absorbance at 610 nm following vortex. For the main culture suspended cells were inoculated to reach 1.5 of initial OD into 10 ml of the production medium contained in an autoclaved 100 ml of Erlenmeyer flask having 0.5 g of $CaCO_3$. Main culture was performed on a rotary shaker (Infors AJ118, Bottmingen, Switzerland) with 200 rpm for 48-78 hours at 30° C. The concentrations of cadaverine and lysine were determined using HPLC (Agilent 1100 Series LC system).

In the broth cultured with all recombinant strains containing the lysine decarboxylase genes a significant amount of cadaverine was accumulated. On the contrary, marked decrease in the lysine productivity was observed. Considering complete conversion of lysine to cadaverine the same number of cadaverine molecules as lysine must be produced. However, the amount of cadaverine accumulated was less than that of lysine produced by host strain, on the other hand, a considerable amount of byproduct, acetylcadaverine, was concomitantly accumulated resulting in sugar yield decrease. In addition to HPLC analysis, cadaverine and acetylcadaverine were identified by mass spectrometrical method.

4. Identification of the Acetylcadaverine-Forming Enzyme

To identify the acetylcadaverine-forming enzyme protein purification was performed. The *C. glutamicum* strain ATCC13032 or of some derivatives cultured in CM liquid were harvested, washed and suspended in 0.5 volume of standard buffer consisting of 50 mM Tris-HCl (pH 7.8), 0.02% Brij 35, protein inhibitor mix (Complete, Roche) and 20% glycerol. Cell suspension was disrupted using Microfluidizer (M–110EH, Microfluidics Co.) followed by filtration using Microfiltrater (MF42, Satorius).

The enzyme in the filtrate was purified by applying to a series of columns of Q Sepharose (Amersham Bioscience, 50×300 mm, linear gradient of 0.0-0.5 M-NaCl in 10 mM Tris (pH 7.5) buffer, 10 ml/min of flow rate), Phenyl Sepharose (Amersham Bioscience, 50×300 mm, linear gradient of 1.5-0.0 M-ammonium acetate in 10 mM Tris (pH 7.5) buffer, 10 ml/min of flow rate), Superdex (Amersham Bioscience, 26×600 mm, 10 mM Tris (pH 7.5) buffer, 4 ml/min of flow rate), Mono-Q (Amersham Bioscience, 5×50 mm, linear gradient of 0.0-0.5 M-NaCl in 10 mM Tris (pH 7.5) buffer, 1 ml/min of flow rate) and Superose (Amersham Bioscience, 15×300 mm, 10 mM Tris (pH 7.5) buffer, 0.3 ml/min of flow rate). All through the purification steps enzyme activity of the acetyltransferase in the fractions and the presence of acetylcadaverine in the mixture of enzyme reactions were monitored. Enzyme activity was determined by monitoring increase of absorption at 412 nm due to the generation of TNB (thionitrobenzoic acid) in a total volume of 1 ml under the following conditions:

10 mM Tris-HCl (pH 7.8), 0.1 mM DTNB (5,5'-dithiobis-(2-nitrobenzoic acid)), 0.25 mM acetyl CoA, 5 mM cadaverine, enzyme solution Specific activities were calculated using the molar extinction coefficient of 13.6 mM$^{-1}$×cm$^{-1}$ for TNB.

The fractions containing enzyme activity from Superose column were loaded on SDS-PAGE gel. The protein spots were digested with modified trypsin (Roche, Mannheim) as described by Hermann et al. (Electrophoresis (2001), 22, 1712-1723) following excising from Coomassie-stained gel. Mass spectrometrical identifications were performed on an LCQ advantage (Thermo Electron) after nano-HPLC separation of the peptides (LC Packings, RP18 column, length 15 cm, i.d. 75 μm), using the MASCOT software (David et al. (1999) Electrophoresis, 20, 3551-3567). Consequently, an acetyltransferase (Genebank accession number: NP_600742) was identified as a potential acetylcadaverine-forming enzyme.

5. Plasmid Construction and Disruption of the Acetyltransferase Gene

For the chromosomal disruption of the gene encoding the acetyltransferase identified a recombinant plasmid was constructed which allows the marker-free manipulation by two consecutive homologous recombination events. The DNA fragments containing the regions of the up- and the downstream of the gene were amplified from *C. glutamicum* chromosomal DNA using a sets of PCR primers, WKJ203/WKJ205 for the upstream and WKJ206/WKJ204 for the downstream, and used as a template for fusion PCR with PCR primers WKJ203/WKJ204 to make fused fragment that the middle region of the gene is removed. The product of the fusion PCR was purified, digested with XhoI and SpeI, and inserted into the pClikintsacB vector, which makes the integration of sequences at the genomic locus of *C. glutamicum* (Becker et al (2005), Applied and Environmental Microbiology, 71 (12), p. 8587-8596), digested with same restriction enzymes.

The plasmid was then used to disrupt the native coding region of the acetyltransferase gene. The strain used was LU11271 LdcC in which the ldcC gene was integrated into the bioD locus of the chromosome and which produces both cadaverine and acetylcadaverine. Two consecutive recombination events, one in each of the up- and the down-stream region, respectively, are necessary to disrupt the middle sequence of the gene. The disrupted mutants were confirmed by PCR with primers WKJ203/WKJ204 and Southern hybridization analysis.

Oligonucleotide Primers Used:

WKJ203  gctcctcgaggcattgtatactgcgaccact
        (SEQ ID NO: 10)

WKJ204  cggtactagtgtagtgagccaagacatgg
        (SEQ ID NO: 11)

WKJ205  cgattccgtgattaagaagcgcttcaaccagaacatcgac
        (SEQ ID NO: 12)

WKJ206  gtcgatgttctggttgaagcgcttcttaatcacggaatcg
        (SEQ ID NO: 13)

6. Effect on Acetylcadaverine Formation and Cadaverine Productivity

To analyze the effect of the disruption of the acetyltransferase gene on acetylcadaverine formation and cadaverine productivity, shaking flask experiments were performed on the disrupted mutants. The same culture medium and conditions as cadaverine production were used (vide supra). The disrupted mutants showed no accumulation of acetylcadaverine. This indicates that only the acetyltransferase identified is responsible for the acetylcadaverine formation. Consequently, cadaverine productivity was improved by disruption of the gene resulting in elimination of acetylcadaverine formation.

The gene sequence and the polypeptide sequence of acetyltransferase is disclosed below:

Acetyltransferase gene sequence (SEQ ID NO: 14)
ATGAGTCCCACCGTTTTGCCTGCTACACAAGCTGACTTCCCTAAGATCGT
C-GATGTTCTGGTTGAAGCATTCGCCAACGATCCAGCATTTTTACGATGG

```
ATCCCG-CAGCCGGACCCCGGTTCAGCAAAGCTTCGAGCACTTTTCGAAC

TGCAGATTGAGAAG-CAGTATGCAGTGGCGGGAAATATTGATGTCGCGCG

TGATTCTGAGGGAGA-AATCGTCGGCGTCGCGTTATGGGATCGGCCAGAT

GGTAATCACAGTGCCAAAGAT-CAAGCAGCGATGCTCCCCCGGCTCGTCT

CCATTTTCGGGATCAAGGCTGCG-CAGGTGGCGTGGACGGATTTGAGTTC

GGCTCGTTTCCACCCCAAATTCCCCCATTGG-TACCTCTACACCGTGGCA

ACATCTAGTTCTGCCCGTGGAACGGGTGTTGG-CAGTGCGCTTCTTAATC

ACGGAATCGCTCGCGCGGGTGATGAAGCTATCTATTTG-GAGGCGACGTC

GACTCGTGCGGCTCAACTATATAACCGTCTGG-GATTTGTGCCCTTGGGT
```

```
TATATCCCCTCAGATGATGATGGCACTCCTGAACTGGC-GATGTGGAAAC

CGCCAGCGATGCCAACTGTTTAA
```

Protein sequence (SEQ ID NO: 15)
MSPTVLPATQADFPKIVDVLVEAFANDPAFLRWIPQPDPGSAKLRALFEL
QIEKQYA-VAGNIDVARDSEGEIVGVALWDRPDGNHSAKDQAAMLPRLVS
IFGIKAAQVAWTDLS-SARFHPKFPHWYLYTVATSSSARGTGVGSALLNH
GIARAGDEAIYLEATSTRAAQ-LYNRLGFVPLGYIPSDDDGTPELAMWKP
PAMPTV

---

The invention claimed is:

1. A recombinant microorganism of the genus *Corynebacterium* which has a deregulated lysine decarboxylase gene and a deregulated diamine acetyltransferase gene and at least one deregulated gene (i) selected from the group consisting of up-regulated aspartokinase, up-regulated aspartatesemialdehyde dehydrogenase, up-regulated dihydrodipicolinate synthase, up-regulated dihydrodipicolinate reductase, up-regulated tetrahydrodipicolinate succinylase, up-regulated succinyl-amino-ketopimelate transaminase, up-regulated succinyl-diamino-pimelate desuccinylase, up-regulated diaminopimelate epimerase, up-regulated diaminopimelate dehydrogenase, up-regulated arginyl-tRNA synthetase, up-regulated diaminopimelate decarboxylase, up-regulated pyruvate carboxylase, up-regulated phosphoenolpyruvate carboxylase, up-regulated glucose-6-phosphate dehydrogenase, up-regulated transketolase, up-regulated transaldolase, up-regulated 6-phosphogluconolactonase, up-regulated fructose 1,6-biphosphatase, down-regulated homoserine dehydrogenase, down-regulated phophoenolpyruvate carboxykinase, down-regulated succinyl-CoA synthetase, and down-regulated methylmalonyl-CoA mutase, provided that if aspartokinase is deregulated as the at least one deregulated gene (i), at least a second gene (i) other than aspartokinase has to be deregulated, wherein the deregulated diamine acetyltransferase gene is from *Corynebacterium*.

2. The recombinant microorganism of claim 1, wherein the deregulated lysine decarboxylase gene is from *Escherichia*.

3. The recombinant microorganism of claim 1, wherein the diamine acetyltransferase gene is deleted or disrupted.

4. A process for the production of cadaverine comprising constructing the recombinant microorganism of claim 1 and cultivating said microorganism to produce cadaverine, wherein said microorganism comprises an up-regulated lysine decarboxylase gene, a down-regulated diamine acetyltransferase gene, and an up-regulated aspartokinase gene.

5. The process of claim 4, wherein the microorganism is *Corynebacterium glutamicum*.

6. The process of claim 4, wherein the up regulated lysine decarboxylase is heterologous to said microorganism.

7. The process of claim 4, wherein the up regulated lysine decarboxylase is from *Escherichia*.

8. The process of claim 4, wherein the lysine decarboxylase has the polypeptide sequence of SEQ ID NO: 1 or 2 or a polypeptide sequence with a lysine decarboxylase activity which is at least 80% identical to SEQ ID NO: 1 or 2.

9. A process for the production of a polyamide comprising producing cadaverine according to the process of claim 4 and reacting the cadaverine with a dicarboxylic acid.

10. The recombinant microorganism of claim 1, wherein the microorganism comprises a down-regulated homoserine dehydrogenase gene.

11. The recombinant microorganism of claim 1, wherein the microorganism comprises an up-regulated pyruvate carboxylase gene.

12. The recombinant microorganism of claim 1, wherein the microorganism belongs to the species *Corynebacterium glutamicum*.

13. The recombinant microorganism of claim 1, wherein said microorganism accumulates less acetylcadaverine as compared to a corresponding microorganism without said deregulated diamine acetyltransferase gene.

14. A recombinant microorganism of the genus *Corynebacterium* comprising a deregulated lysine decarboxylase gene and a deregulated diamine acetyltransferase gene and at least one deregulated gene (i) selected from the group consisting of aspartokinase, aspartatesemialdehyde dehydrogenase, dihydrodipicolinate synthase, dihydrodipicolinate reductase, tetrahydrodipicolinate succinylase, succinyl-amino-ketopimelate transaminase, succinyl-diamino-pimelate desuccinylase, diaminopimelate epimerase, diaminopimelate dehydrogenase, arginyl-tRNA synthetase, diaminopimelate decarboxylase, pyruvate carboxylase, phosphoenolpyruvate carboxylase, glucose-6-phosphate dehydrogenase, transketolase, transaldolase, 6-phosphogluconolactonase, fructose 1,6-biphosphatase, homoserine dehydrogenase, phophoenolpyruvate carboxykinase, succinyl-CoA synthetase, and methylmalonyl-CoA mutase, provided that if aspartokinase is deregulated as the at least one deregulated gene (i), at least a second gene (i) other than aspartokinase has to be deregulated, wherein the diamine acetyltransferase prior to deregulation comprises the sequence of SEQ ID NO: 15 or is encoded by the sequence of SEQ ID NO: 14.

15. The recombinant microorganism of claim 14, wherein said microorganism accumulates less acetylcadaverine as compared to a corresponding microorganism without said deregulated diamine acetyltransferase gene.

* * * * *

SEQUENCE LISTING

<160> NUMBER OF SEQ ID NOS: 15

<210> SEQ ID NO 1
<211> LENGTH: 715
<212> TYPE: PRT
<213> ORGANISM: Escherichia coli

<400> SEQUENCE: 1

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

```
Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
            370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
            595                 600                 605

Ala Phe Glu Val Leu Pro Thr Met Val Met Thr Pro Tyr Ala Ala Phe
            610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
```

```
                675                 680                 685
Phe Glu Thr Asp Ile His Gly Ala Tyr Arg Gln Ala Asp Gly Arg Tyr
        690                 695                 700

Thr Val Lys Val Leu Lys Glu Ser Lys Lys
705                 710                 715

<210> SEQ ID NO 2
<211> LENGTH: 713
<212> TYPE: PRT
<213> ORGANISM: Escherichia coli

<400> SEQUENCE: 2

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
    290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
```

```
                   340                 345                 350
Arg Val Ala Gly Lys Val Ile Phe Glu Thr Gln Ser Thr His Lys Met
            355                 360                 365
Leu Ala Ala Leu Ser Gln Ala Ser Leu Ile His Ile Lys Gly Glu Tyr
        370                 375                 380
Asp Glu Glu Ala Phe Asn Glu Ala Phe Met Met His Thr Thr Thr Ser
385                 390                 395                 400
Pro Ser Tyr Pro Ile Val Ala Ser Val Glu Thr Ala Ala Ala Met Leu
                405                 410                 415
Arg Gly Asn Pro Gly Lys Arg Leu Ile Asn Arg Ser Val Glu Arg Ala
            420                 425                 430
Leu His Phe Arg Lys Glu Val Gln Arg Leu Arg Glu Glu Ser Asp Gly
        435                 440                 445
Trp Phe Phe Asp Ile Trp Gln Pro Pro Gln Val Asp Glu Ala Glu Cys
    450                 455                 460
Trp Pro Val Ala Pro Gly Glu Gln Trp His Gly Phe Asn Asp Ala Asp
465                 470                 475                 480
Ala Asp His Met Phe Leu Asp Pro Val Lys Val Thr Ile Leu Thr Pro
                485                 490                 495
Gly Met Asp Glu Gln Gly Asn Met Ser Glu Gly Ile Pro Ala Ala
            500                 505                 510
Leu Val Ala Lys Phe Leu Asp Glu Arg Gly Ile Val Val Glu Lys Thr
        515                 520                 525
Gly Pro Tyr Asn Leu Leu Phe Leu Phe Ser Ile Gly Ile Asp Lys Thr
    530                 535                 540
Lys Ala Met Gly Leu Leu Arg Gly Leu Thr Glu Phe Lys Arg Ser Tyr
545                 550                 555                 560
Asp Leu Asn Leu Arg Ile Lys Asn Met Leu Pro Asp Leu Tyr Ala Glu
                565                 570                 575
Asp Pro Asp Phe Tyr Arg Asn Met Arg Ile Gln Asp Leu Ala Gln Gly
            580                 585                 590
Ile His Lys Leu Ile Arg Lys His Asp Leu Pro Gly Leu Met Leu Arg
        595                 600                 605
Ala Phe Asp Thr Leu Pro Glu Met Ile Met Thr Pro His Gln Ala Trp
    610                 615                 620
Gln Arg Gln Ile Lys Gly Glu Val Glu Thr Ile Ala Leu Glu Gln Leu
625                 630                 635                 640
Val Gly Arg Val Ser Ala Asn Met Ile Leu Pro Tyr Pro Pro Gly Val
                645                 650                 655
Pro Leu Leu Met Pro Gly Glu Met Leu Thr Lys Glu Ser Arg Thr Val
            660                 665                 670
Leu Asp Phe Leu Leu Met Leu Cys Ser Val Gly Gln His Tyr Pro Gly
        675                 680                 685
Phe Glu Thr Asp Ile His Gly Ala Lys Gln Asp Glu Asp Gly Val Tyr
    690                 695                 700
Arg Val Arg Val Leu Lys Met Ala Gly
705                 710

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
```
caagctcctt cgagctggca                                           20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gggtaacgta aaccagagaa                                           20

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
gagagagact cgagtagctg ccaattattc cggg                           34

<210> SEQ ID NO 6
<211> LENGTH: 40
<212> TYPE: DNA
<213> ORGANISM: Artificial Sequence
<220> FEATURE:
<223> OTHER INFORMATION: Primer

<400> SEQUENCE: 6
acgaaaggat tttttaccca tgaacatcat tgccattatg                     40

<210> SEQ ID NO 7
<211> LENGTH: 35
<212> TYPE: DNA
<213> ORGANISM: Artificial Sequence
<220> FEATURE:
<223> OTHER INFORMATION: Primer

<400> SEQUENCE: 7
ctctctctca ctagtgctca atcacatatt gccca                          35

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
gagagagact cgagccggaa gcgatggcgg catc                           34

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
gggtaaaaaa tcctttcgta g                                         21

<210> SEQ ID NO 10
<211> LENGTH: 31
<212> TYPE: DNA
<213> ORGANISM: Artificial Sequence

```
<220> FEATURE:
<223> OTHER INFORMATION: Primer

<400> SEQUENCE: 10
gctcctcgag gcattgtata ctgcgaccac t                              31

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
cggtactagt gtagtgagcc aagacatgg                                 29

<210> SEQ ID NO 12
<211> LENGTH: 40
<212> TYPE: DNA
<213> ORGANISM: Artificial Sequence
<220> FEATURE:
<223> OTHER INFORMATION: Primer

<400> SEQUENCE: 12
cgattccgtg attaagaagc gcttcaacca gaacatcgac                     40

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
gtcgatgttc tggttgaagc gcttcttaat cacggaatcg                     40

<210> SEQ ID NO 14
<211> LENGTH: 612
<212> TYPE: DNA
<213> ORGANISM: Corynebacterium glutamicum

<400> SEQUENCE: 14
atgagtccca ccgttttgcc tgctacacaa gctgacttcc ctaagatcgt cgatgttctg    60
gttgaagcat cgccaacga tccagcattt ttacgatgga tcccgcagcc ggaccccggt   120
tcagcaaagc ttcgagcact tttcgaactg cagattgaga agcagtatgc agtggcggga   180
aatattgatg tcgcgcgtga ttctgaggga gaaatcgtcg gcgtcgcgtt atgggatcgg   240
ccagatggta atcacagtgc caaagatcaa gcagcgatgc tccccggct cgtctccatt   300 ttcgggatca aggctgcgca ggtggcgtgg acgatttga gttcggctcg tttccacccc   360
aaattccccc attggtacct ctacaccgtg gcaacatcta gttctgcccg tggaacgggt   420
gttggcagtg cgcttcttaa tcacggaatc gctcgcgcgg gtgatgaagc tatctatttg   480
gaggcgacgt cgactcgtgc ggctcaacta tataaccgtc tgggatttgt gcccttgggt   540
tatatcccct cagatgatga tggcactcct gaactggcga tgtggaaacc gccagcgatg   600
ccaactgttt aa                                                       612

<210> SEQ ID NO 15
<211> LENGTH: 203
<212> TYPE: PRT
<213> ORGANISM: Corynebacterium glutamicum

<400> SEQUENCE: 15
```

```
Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
                20                  25                  30

Trp Ile Pro Gln Pro Asp Pro Gly Ser Ala Lys Leu Arg Ala Leu Phe
            35                  40                  45

Glu Leu Gln Ile Glu Lys Gln Tyr Ala Val Ala Gly Asn Ile Asp Val
        50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
            115                 120                 125

Thr Val Ala Thr Ser Ser Ala Arg Gly Thr Gly Val Gly Ser Ala
        130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Asp Gly Thr Pro Glu Leu
            180                 185                 190

Ala Met Trp Lys Pro Pro Ala Met Pro Thr Val
            195                 200
```